United States Patent [19]

Lee et al.

[11] Patent Number: 4,917,895
[45] Date of Patent: Apr. 17, 1990

[54] TRANSDERMAL DRUG DELIVERY DEVICE

[75] Inventors: Eun S. Lee, Redwood City; David Edgren, El Granada; Su I. Yum, Los Altos, all of Calif.

[73] Assignee: ALZA Corporation, Palo Alto, Calif.

[21] Appl. No.: 219,115

[22] Filed: Jul. 14, 1988

Related U.S. Application Data

[63] Continuation-in-part of Ser. No. 115,949, Nov. 2, 1987, abandoned.

[51] Int. Cl.$^4$ ............................................. A61F 13/02
[52] U.S. Cl. ................................... 424/448; 424/449
[58] Field of Search ............................. 424/448, 449

[56] References Cited

U.S. PATENT DOCUMENTS

| | | | |
|---|---|---|---|
| 3,598,122 | 8/1971 | Zaffaroni | 128/268 |
| 3,598,123 | 8/1971 | Zaffaroni | 128/268 |
| 3,870,593 | 3/1975 | Elton et al. | 161/159 |
| 3,923,939 | 12/1975 | Baker et al. | 264/49 |
| 4,012,221 | 3/1977 | Walker et al. | 71/66 |
| 4,144,317 | 3/1979 | Higuchi et al. | 424/21 |
| 4,166,111 | 8/1979 | Cardarelli | 424/78 |
| 4,177,256 | 12/1979 | Michaels et al. | 424/22 |
| 4,286,592 | 9/1981 | Chandrasekaran | 128/260 |
| 4,314,557 | 2/1982 | Chandrasekaran | 128/260 |
| 4,379,454 | 4/1983 | Campbell et al. | 604/897 |
| 4,568,343 | 2/1986 | Leeper et al. | 604/896 |
| 4,655,766 | 4/1987 | Theeuwes et al. | 604/896 |
| 4,661,105 | 4/1987 | Gale | 604/897 |

FOREIGN PATENT DOCUMENTS

0197504A2  10/1986  European Pat. Off.

OTHER PUBLICATIONS

Dix et al, "The Resistance of Aluminum Alloys to Corrosion," METALS HANDBOOK VI (8th ed.), p. 916.
E. W. Horvick, "The Use of Zinc in Corrosion Service," METALS HANDBOOK VI (8th ed.), p. 1162.
ASM Committee on Magnesium, "The Corrosion of Magnesium Alloys," METALS HANDBOOK VI (8th ed.), p. 1086.
Hemingway et al, "The Dissolution of Metallic Nickel in Artificial Sweat," CONTACT DERMATITIS, 16, pp. 99–105 (1987).
Van Nostrand Reinhold Encyclopedia of Chemistry, Fourth Edition, "Metals," pp. 569–570 (1984).
The Encyclopedia of Chemistry, Second Edition, ed. George L. Clark, "Metals," pp. 643–648 (1966).

*Primary Examiner*—Thurman K. Page
*Assistant Examiner*—Leon R. Horne
*Attorney, Agent, or Firm*—Steven F. Stone; Edward L. Mandell; Paul L. Sabatine

[57] ABSTRACT

A diffusional drug delivery device is described which can provide shelf life stability of the system components, elimination of the initial burst of drug and hence irritation, delayed onset of therapeutic effect and delivery of a therapeutic agent at an optimum rate. A metal layer and an activating means are inert when dry. Moisture activates the system whereby the activating means provides release of an eroding agent which erodes the metal layer through which the therapeutic agent diffuses and is subsequently delivered.

16 Claims, 3 Drawing Sheets

TRANSDERMAL DRUG DELIVERY DEVICE

RELATED PATENT APPLICATIONS

This application is a continuation in part of coassigned patent application Ser. No. 07/115,949 filed Nov. 2, 1987, now abandoned which is incorporated herein and benefit is claimed of its filing date.

This application is related to the copending, coassigned patent application Ser. No. 07/022,301, filed March 5, 1987 entitled "Delayed Onset Transdermal Drug Delivery Device", which in turn is a continuation of patent application Ser. No. 06/874,263, filed June 13, 1986, of the same title.

FIELD OF THE INVENTION

This invention relates to the transdermal delivery of drugs or other biologically active agents and particularly to novel methods and compositions for providing stable systems under storage conditions. Still more particularly, this invention relates to novel methods and compositions for delaying the onset of drug delivery for transdermal systems.

BACKGROUND OF THE INVENTIONS

The transdermal route of parenteral delivery of drugs provides many advantages and transdermal systems for delivering a wide variety of drugs or other beneficial agents are described in U.S. Pat. Nos. 3,598,122, 3,598,123, 4,286,592, 4,314,557, 4,379,454 and 4,568,343 for example, all of which are incorporated herein by reference.

In these devices, a drug or other active agent is released by diffusion from a reservoir through the agent releasing surface of the device to the biological environment at which the device is applied. Such devices perform well in the administration of many agents but are not suitable for the administration of an agent whose dosage regime requires that the onset of therapeutic effect be delayed for a significant period of time after application of the device at the site of delivery. This is because the concentration of the active agent at the surface through which the agent is released, at the time of application, is typically at or above saturation and is capable of delivering at a rate that can give rise to therapeutic blood levels. In some cases, the initial rate of release is unacceptably high and a method for reducing this initial "burst" of agent delivery is described in U.S. Pat. No. 3,923,939 to Baker et al. Even in this patent, the agent releasing surface of the diffusional embodiment does contain agent and delivery commences immediately in the manner described above.

Non-diffusional devices are known which do not immediately present drug to the biological environment when installed, such as devices which contain material in breakable microcapsules, or fluid imbibing pumps, such as that described in U.S. Pat. No. 4,655,766 of Theeuwes et al. Diffusional delivery devices known to the art however, do not possess this capability.

The devices of this invention are particularly useful in providing a predetermined delayed onset of therapeutic effect for any desired time period after application to the skin. Thus a device could be removed and a new one applied simultaneously, wherein the desired drug-free interval is obtained.

One of the advantages of a continuous release dosage form, such as a transdermal drug delivery device, is the improvement in patient compliance that is obtained from the concurrent removal of one device and application of a new device at the same time. This advantage is lost when removal and application occur at different times or where onset of a therapeutic effect is desired at an inconvenient time such as shortly prior to arousal from sleep. It is not possible, using concurrent application and removal of diffusional delivery devices known in the art, to substantially delay the onset of transdermal drug delivery from the time of application, such as bedtime, until shortly prior to arousal.

Additionally, a common problem encountered with state of the art systems is how to deal with unstable active agents, especially those that tend to degrade the adhesive and other system components. Therefore, there is a continuing need for a transdermal therapeutic system that provides stability of the active agent and all components during storage.

SUMMARY OF THE INVENTION

An object of this invention is to provide a diffusional agent delivery device which provides for delayed onset of agent administration.

A further object of this invention is to provide a diffusional drug delivery device which does not deliver an initial burst of drug and hence is less likely to cause irritation.

Another object of this invention is to provide a diffusional delivery system where the adhesive and other components are protected by use of a metal layer which acts to retain the active agent within its reservoir, thus preventing it from coming into contact with the other components during storage.

A further object of this invention is to provide for the maintenance of drug potency and device efficacy during prolonged storage periods, whereby the device is inactive while stored, and active when applied to the skin.

A still further object of this invention is to provide a diffusional delivery device which continuously releases therapeutic agent into a biological environment after a period of no drug delivery.

These and other objects, features, and advantages have been demonstrated by the present invention wherein a controlled release medical device for delivery of a drug in a predetermined delivery rate pattern to a biological environment is comprised of, in combination: reservoir means containing drug and having a surface through which the drug is released to the biological environment; a metal layer disposed between the reservoir means and the biological environment, wherein said metal layer in a first state, is substantially impermeable to the passage of said drug and in a second state is permeable to said drug: and activating means by which the metal layer is changed from said first to said second state; whereby substantially all of the drug dose must pass through the metal layer to reach the biological environment, and whereby the passage of drug to the biological environment by diffusion is impeded until the metal layer changes state.

BRIEF DESCRIPTION OF THE DRAWINGS

In the drawings, which are not drawn to scale, but rather are set forth to illustrate the various embodiments of the invention and wherein like reference numerals designate like parts, the drawings are as follows.

DESCRIPTION OF THE PREFERRED EMBODIMENT

The transdermal drug delivery system of this invention is designed to delay drug delivery and to control the initial excess burst of drug. In this manner, a means for delayed onset is provided which gives a drug-free period in plasma during continuous application of a transdermal drug delivery system.

More importantly, this invention provides the distinct advantage of improved shelf life stability. It serves this purpose by storing a drug in a system having a metal layer which, in a first state, acts as a barrier to the passage of drug. In this manner, not only is the initial "burst" avoided, but also the drug does not come into contact with the other system components during storage. This is advantageous since many active agents have a tendency to degrade system components upon prolonged exposure. State of the art devices use polymer films as diffusion barriers. The diffusion coefficients of drugs in metals are much smaller than those of drugs in polymers. Therefore, the metallic film utilized by the system of this invention provides a more stable barrier than a polymer film; and thus, the drug is better retained within its reservoir during the storage period.

An additional advantage of a metal barrier is the sharp onset of drug delivery attained. As a polymer barrier changes from being substantially impermeable to permeable to the passage of drug, drug gradually diffuses through, i.e. the drug has a long diffusional time lag. Once the permeable state is attained, drug can diffuse through at a therapeutic rate, i.e. the drug then has a short diffusional time lag. As the metal barrier is changing state, drug does not diffuse through. Once the metal is eroded, the drug can immediately pass at a therapeutic rate. Therefore, unlike the situation with the polymer films, there is no gradual buildup of drug. With a metal film, drug delivery has a sharp onset.

With reference to the Figures, the devices shown represent for purposes of illustration, transdermal delivery devices because these are the preferred embodiments of this invention. It must be recognized however, that this invention is applicable to delivery devices generally and in non-transdermal applications, certain components such as the adhesive and backing layers can be omitted. A transdermal delivery device according to this invention may include an impermeable backing member, a therapeutic agent reservoir, a metal layer which in a first state is substantially impermeable to the drug and in a second state is permeable to the drug, and an activating means containing an eroding agent, whereby the metal layer is converted from its first to its second state.

It is believed that this invention has utility in connection with the delivery of drugs within the broad class normally delivered through body surfaces and membranes, including skin. As used herein, the expressions "drug", "active agent" and "therapeutic agent" are used interchangeably and are intended to have their broadest interpretation as any therapeutically active substance which is delivered to a living organism to produce a desired, usually beneficial, effect. In general, this includes therapeutic agents in all of the major therapeutic areas including, but not limited to, those disclosed in the aforementioned patents.

This invention also finds utility in connection with the delivery of drugs such as benztropine, nicotine and secoverine. These drugs tend to degrade the components of the system, including the adhesive, upon prolonged exposure such as is the case under storage conditions. By using a metal barrier to keep the drug in its reservoir during storage, the degradation problem is avoided.

As stated above, this invention provides delayed onset of drug delivery. This is useful in the delivery of drugs such as nitroglycerin where a typical regimen involves concurrent application and removal of transdermal delivery systems and delivery from the freshly applied system is not immediately desired.

This invention also eliminates any initial burst of drug. This is particularly beneficial in delivering drugs that have a tendency in large doses, to irritate the skin. These drugs include benztropine, secoverine and nicotine, as noted above, along with beta-blockers such as propranolol and timolol.

A diffusional delivery device, in its broadest sense, comprises an agent reservoir from which agent passes by diffusion to the agent releasing surface of the device and from there into the biological environment to which it is applied.

In the preferred embodiment of this invention, a metal layer and an activating means are disposed between the drug reservoir and the surface through which the drug is released from the device to produce a delayed onset of drug administration at the intended therapeutic rate. The activating means is substantially free of undissolved drug. The metal layer is disposed between the drug reservoir and the activating means. Delayed drug delivery is attainable as the metal layer in a first dry and un-eroded state has a low permeability, and in a second eroded state, the metal is eroded and thus has a high permeability to the drug whose release is being delayed. Typically, there will be at least a factor of two, and preferably at least an order of magnitude difference in permeability between the first and second states.

In the preferred embodiment, a water-based reaction(s) triggers the change of state. In order to prevent premature erosion of the metal layer, the system is maintained in an anhydrous environment prior to use. Within these broad limitations, the specific structure of the drug delivery device is not critical to this invention.

This invention possesses unique characteristics by which it may readily be distinguished from other diffusional delivery devices. As noted above, when conventional diffusional devices are placed into operation, the concentration of the agent at the agent releasing surface is absorbed by the body. According to certain embodiments of our invention, however, the concentration of the agent at the agent releasing surface actually increases after the device is placed into operation. This occurs because the activating means functions to maintain the initial concentration of the agent at the agent releasing surface of the device substantially below the concentration which will exist when the device is operating at its intended steady state agent delivery rate. It should be noted that this can also be achieved with a membrane which delays agent delivery but does not undergo a change in state. Such a system is disclosed in the copending, coassigned patent application of Urquhart et al, Serial No. 06/874,262 filed June 13, 1986 entitled Delayed Onset Delivery Device, which is incorporated herein by reference.

Figure 1:
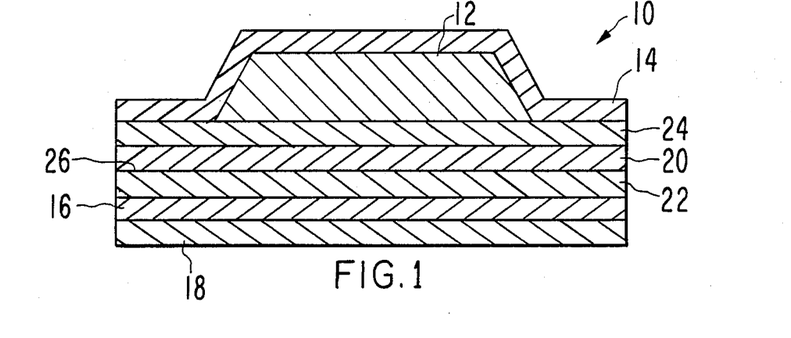
FIG. 1 is a schematic cross-sectional view of one embodiment of the transdermal drug delivery system of this invention.

The transdermal drug delivery system of this invention is best described with relation to FIG. 1. The system 10 is comprised of a drug reservoir 12 which is comprised of a drug dispersed within a matrix which may or may not be anhydrous, either as a solid, liquid or gel, or mixed with suitable carriers. The drug reservoir 12 may also contain stabilizing agent, thickeners, permeation enhancers or other additives well known in the art. The devices are preferably in the form of an adhesive patch or the like, but can also be in a form suitable for application to the skin or mucosa, such as an ointment, gel or matrix, for example. If desired, means for controlling the release rate can also be used, as is known in the art.

In a preferred embodiment, reservoir 12 is covered by an impermeable backing 14. The system 10 is held in place by means of an in-line pharmaceutically acceptable contact adhesive 16. A strippable release liner 18, adapted to be removed prior to application would normally be included in the packaged product. The system 10 is further comprised of a metal layer 20, an activating means 22 and a rate controlling membrane 24. The various layers are laminated or otherwise assembled into a bandage having a predetermined size and shape as is known to the art.

The polymer matrix of the activating means is anhydrous and may be either a solid, or a non-aqueous liquid or gel, or it can be mixed with suitable anhydrous carriers. The activating means may also contain additives as are known in the art. Particularly useful is the addition of a drying agent to ensure that moisture does not prematurely activate the system. Suitable materials include without limitation, natural and synthetic rubbers or other polymeric materials, thickened mineral oil or petroleum jelly.

Various materials suited for the fabrication of the various layers are disclosed in the aforementioned patents. The preferred embodiment according to this invention is fabricated from an ethylene vinylacetate (EVA) copolymer of the type described in U.S. Pat. No. 4,144,317, preferably those having a vinylacetate content in the range of about 28 to 60 weight percent. Particularly good results have been obtained using an EVA copolymer of about 40 weight percent vinylacetate content (40 w% VA). The drug and eroding agent are preferably dispersed through their respective matrices at a concentration in excess of saturation, the amount of excess being a function of the intended useful life of the system. In addition to the drug and eroding agent, the drug reservoir and activating means may also contain other materials such as dyes, pigments, inert fillers, permeation enhancers, excipients and conventional components of pharmaceutical products or transdermal therapeutic systems as is known to the art.

Rate controlling membrane 24 may be fabricated from permeable, semipermeable or microporous materials which are known in the art to control the rate of agents or fluids into and out of delivery devices. Suitable materials include, without limitation, polyvinylacetate and ethylene vinylacetate. The function of membrane 24 is to control the rate at which drug leaves the device, more specifically, the rate at which the drug passes from reservoir 12. Therefore, membrane 24 is preferably of a material such that the in vitro flux of the drug across it is less than the in vitro flux of drug through the skin. However, this invention also contemplates use of a membrane whose in vitro drug flux is equal to or greater than that of the skin.

System 10 can also operate without rate controlling membrane 24. In that instance, the metal layer 20 would act as the rate control. When eroded by the activating means 22, pits can form in the metal layer. These pits then act as pathways for the diffusion of drug. Thus, in effect the metal layer can perform as a rate controlling microporous membrane.

As used herein, the expression "changes state" refers to the change occurring to the metal layer where in a first state, the metal is a barrier to drug diffusion and in a second state, it allows drug to diffuse through. The term "erosion" is used herein to define various processes that can result in this change of state. Therefore, "erosion" is interpreted broadly to include, without limitation, corrosion, oxidation, dissolution, disintegration and electrolytic reactions.

Many chemical processes are characterized by the transfer of electrons between the reacting species. These are known as oxidation-reduction reactions. The delay or pulsed drug delivery attainable by our invention is preferably based upon this process, where the eroding agent contained within the activating means, acts as an oxidizing agent. Oxidation involves the loss of electrons by a substance and reduction is the process whereby electrons are gained. In any oxidation-reduction reaction, the ratio of moles of substance oxidized to moles of substance reduced is such that the number of electrons lost by one species is equal to the number gained by the other.

The tendency of various substances to gain or lose electrons differs immensely. Those substances possessing a strong affinity for electrons cause other substances to be oxidized by abstracting electrons from them. Reagents that function in this manner are called oxidizing agents. In acting as an oxidizing agent, the substance itself is reduced. On the other hand, reducing agents are substances that readily give up electrons, thereby causing some other species to be reduced. In this process, the reducing agent is itself oxidized. The relative oxidation tendency is defined by the oxidation potential, a value assigned based upon a scale where the oxidation potential of hydrogen is arbitrarily assigned a value of zero. A substance having a high oxidation potential is easily ionized by oxidizing agents. Therefore, a material having both a relatively high oxidation potential and being stable at ambient temperature, is desirable.

Suitable materials for the metal layer are those which are stable when dry, even if in direct contact with an eroding agent. Further, the material should be erodible without adversely affecting the skin. Upon exposure to moisture, however, these materials are readily eroded as they come into contact with the eroding agent in an aqueous environment such as vapor or liquid. The metal layer 20 is formed by thinly coating the rate controlling membrane 24 with a suitable metal. The metal can be coated on by numerous methods which are known in the art, a typical example being vapor deposition.

Suitable materials for the metal layer include without limitation, metals such as magnesium within Group II A, metals such as silver and copper in Group I B and zinc in Group II B, metals such as titanium within Groups III B through VII B inclusive, metals such as iron and nickel in Group VIII, metals such as aluminum in Group III A and tin in Group IV A. These metals are described in detail in the literature. See The Encyclopedia of Chemistry, editor George L. Clark, "Metals," pp. 643-648, Second Edition (1966) and Van Nostrand Reinhold Encyclopedia of Chemistry, editor Douglas M. Considine, "Metals," pp. 569-570, Fourth Edition (1984).

As used herein, the term "metal" is also intended to include alloys. Therefore, the metal layer 20 may also be an alloy of one of the above-listed metals. Alloys offer a high degree of control on the erosion rate and therefore on delay time. Electrode potentials, which are a measure of reactivity, and the erosion rate of alloys by the process of corrosion, have been reported. E. H. Dix Jr., R. H. Brown and W. W. Binger, "The Resistance of Aluminum Alloys to Corrosion", in METALS HANDBOOK VI, 916, American Society of Metals (8th ed). A small change in alloy composition results in a significant change in the erosion rate. For example, 6061 aluminum having 0.6 % iron erodes five times faster than 6061 aluminum having 0.004 % iron. This characteristic can be taken into consideration when selecting an alloy to obtain a specific delay time.

Activating means 22 is comprised of an eroding agent dispersed in a material as disclosed above with reference to the drug reservoir. It is advantageous to control the pH of the activating means, as the erosion rates of metals in aqueous media can be strongly dependent upon pH. By controlling the pH, greater control over the delay time can be achieved. Since a very low or a very high pH may be irritating to the skin, it is preferable to maintain the pH within a biocompatible window of about 2-10. preferably with a pH within the range of about 3-9.

An acidic buffer or weak acid may serve as the eroding agent. A suitable agent is potassium phosphate monobasic ($KH_2PO_4$), whose aqueous solutions have a pH within the range of 4-7. A mildly acidic eroding agent contained within the activating means such as that attained with $KH_2PO_4$ is relatively harmless to human skin, as the natural pH of the human body is itself slightly acidic.

EXAMPLE I

At a pH of 4.5, the corrosion rate of zinc is about 25 mils per year. E. W. Horvick, "The Use of Zinc in Corrosion Service", in METALS HANDBOOK VI, 1162, American Society for Metals (8th ed). In the transdermal drug delivery system of this invention, metal layer 20 would be comprised of a 0.4 micron thick zinc film. At a pH of 4.5, utilizing $KH_2PO_4$ as the eroding agent, this system would theoretically produce a delay time of about 5.6 hours. This is determined by the following equation:

$$\text{delay time} = \text{film thickness/erosion rate}$$

where the erosion rate for a given pH is known. Using the values above, the equation reads:

$$\text{delay time} = \frac{(0.4 \text{ microns})(365 \text{ days/yr})(24 \text{ hrs/day})}{(25 \text{ mil/yr})(25 \text{ microns/mil})}$$

or, $$\text{delay time} = 5.6 \text{ hours}$$

If a longer or a shorter delay time is desired, the film thickness of the metal layer can be adjusted. For example, by decreasing the zinc film thickness to 0.3 microns, the delay time decreases to 4.2 hours. Similarly, the delay time increases to 7.0 hours when a 0.5 micron thick zinc film is utilized. These calculations, given the eroding agent, operating pH and metal layer composition, can be used to calculate the necessary metal layer thickness to attain any desired delay time.

Another suitable eroding agent is sodium bitartrate. This is a weak acid and is especially suitable for use with a magnesium metal layer 20, since it rapidly erodes magnesium when in an aqueous environment. Other suitable eroding agents include, without limitation, citric acid, sodium bisulfate, sodium phosphate monobasic and cupric chloride.

The activating means may, in addition to the eroding agent, also contain small amounts of inorganic salts, to promote erosion of the metal layer.

The salt can be non-oxidizing and acidic such as aluminum sulfate, zinc chloride and sodium acid tartrate; neutral such as sodium chloride and sodium iodide; or alkaline such as sodium borate meta and sodium phosphate. Additionally, the inorganic salt can be oxidizing and acidic such as ammonium persulfate and ferric sulfate; neutral such as sodium chlorate and sodium pyrophosphate; or alkaline such as calcium hypochlorite and sodium iodate. Refer to ASM Committee on Magnesium, "The Corrosion of Magnesium Alloys", in METALS HANDBOOK VI, 1086, American Society for Metals (8th ed).

During storage and when the system 10 is first placed on the patient's skin, the drug is retained within the reservoir 12, as the metal layer 20 is substantially impermeable to the passage of the drug in its first dry and un-eroded state. As a result, the drug releasing surface of certain embodiments of our invention are characterized as being substantially free of drug at the time they are applied to the body. As used herein, the expression "substantially free of drug" means either free of drug or containing an amount of drug insufficient to establish and maintain therapeutically effective rates at the time of application to the delivery site. Therefore, the activating means 22 and adhesive 16 are substantially free of drug.

In accordance with a preferred embodiment of the invention, the activating means 22 is activated by moisture, such as is readily available from the site of administration such as the cutaneous surface, particularly in occluded regions. Means 22 may alternatively be moistened by dipping into a liquid containing vessel immediately prior to application. In operation, this moisture migrates into the system 10 from the skin surface or other source, typically by osmosis or diffusion, passing through the adhesive layer 16 and into the activating means 22, where it mixes with the eroding agent contained therein. The eroding agent hydrates and erodes the metal layer 20 when it comes into contact with the metal layer-activating means interface 26. The drug diffusing through the rate controlling membrane 24 and the eroded metal layer 20, then passes freely through layers 22 and 16 and then through the skin.

One face surface of the drug reservoir bears a backing member 14. The purpose of the backing is to prevent passage of the drug through the surface of the reservoir distant from the adhesive layer. An ancillary purpose of the backing is to provide support for the system, where needed. The backing layer can be flexible or nonflexible and suitable materials include without limitation, cellophane, cellulose acetate, ethylcellulose, plasticized vinylacetate-vinylchloride copolymers, polyethylene terephthalate, nylon, polyethylene, polypropylene, metalized polyester films, polyvinylidene chloride, coated flexible fibrous backings such as paper and cloth and aluminum foil. Such backings can be in the form of precast films or fabrics which are bonded to the reservoir by heat or adhesives and can be coated onto the reservoir. The preferred embodiment utilizes a heat sealable backing membrane, such as that commercially available under the trademark MEDPAR©. Numerous other materials are disclosed in U.S. Pat. No. 4,661,105, incorporated herein by reference.

The composition and thickness of adhesive layer 16 are such that layer 16 does not constitute a significant permeation barrier to the passage of drug. Adhesive layer 16 may also contain a predetermined amount of drug which serves to saturate the skin for more rapid therapeutic effects where desired. Silicone compounds are commonly used as adhesives, however numerous materials are known which possess the requisite strength and skin compatibility. An adhesive overlay or other means for maintaining the device on the skin can be employed instead of, or in combination with, an in-line contact adhesive. Suitable materials are listed in the aforementioned patents.

In operation, release liner 18 is removed and the system is placed in direct contact with the skin. The releaseable liner can be made from materials which are substantially impermeable to the drug, and any other components of the layers. The same materials that are used to make the backing layer may be used to make the liner, provided they are made strippable such as by siliconizing.

The aforementioned patents describe a wide variety of materials which can be used for fabricating the various layers of the transdermal delivery systems according to this invention. This invention therefore, contemplates the use of materials other than those specifically disclosed herein, including those which may hereafter become known to the art to be capable of performing the necessary functions.

Figure 2:
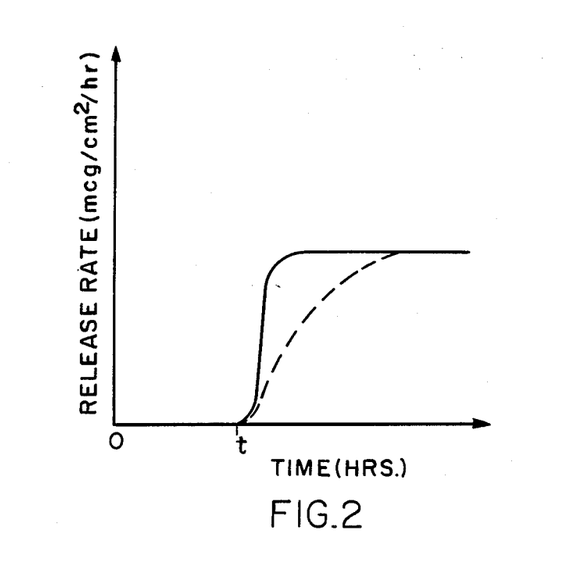
FIG. 2 is a graphic representation of the drug release rate profile of the system illustrated in FIG. 1.

FIG. 2 is a graphical representation of the theoretical release rate profile versus time (solid line) for the system illustrated in FIG. 1. The system 10 is positioned on the skin at time zero. From time zero until time t, moisture from the skin diffuses into the activating means 22 and the eroding agent erodes the the metal layer 20 to allow for passage of the drug contained in reservoir 12, which subsequently diffuses through the layers to reach the skin surface. At time t, the drug begins to actually be delivered into the bloodstream. This is indicated by the rise on the solid line curve in FIG. 2.

The graphical representation of FIG. 2 further provides a comparison between the gradual delayed onset attainable with a polymeric delay layer (dashed line) and the sharp delayed onset attainable with the metal delay layer of this invention (solid line).

Figure 3:
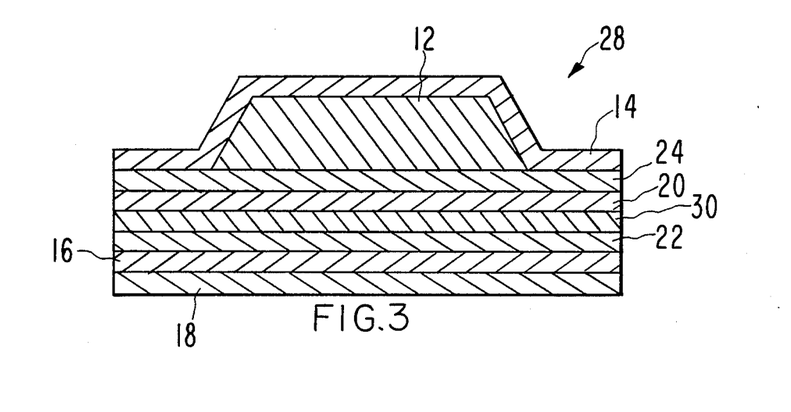
FIG. 3 is a schematic cross-sectional view of another embodiment of this invention, having an eroding agent rate controlling membrane.

An alternate embodiment of the invention is shown in FIG. 3. System 28 is a modification of system 10 (FIG. 1) but has the same basic components and arrangement. The distinction of this embodiment is the presence of an eroding agent rate controlling membrane 30 positioned between the metal layer 20 and the activating means 22. Membrane 30 monitors the flow of eroding agent from the activating means 22 to the metal layer 20, thereby controlling the rate at which the metal layer 20 is eroded. Therefore, while the rate of drug leaving the reservoir is controlled by membrane 24, the actual onset of drug delivery is related to the rate at which the metal layer 20 erodes.

Figure 4:
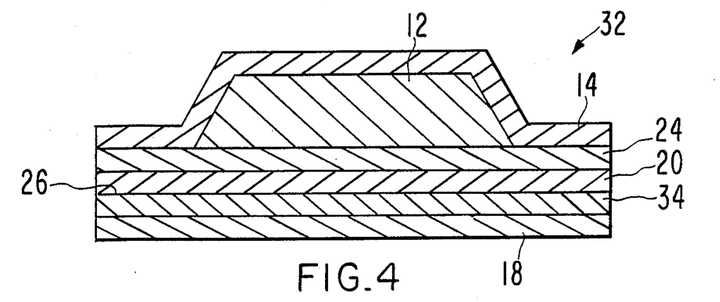
FIG. 4 is a schematic cross-sectional view of another embodiment of this invention, having the eroding agent combined with the adhesive.

Another embodiment of the invention is illustrated in FIG. 4. The distinction of system 32 is that the activating means 34 combines the eroding agent and the in-line contact adhesive in a single layer.

In operation, moisture migrates into the contact adhesive/eroding agent layer 34, resulting in the formation of hydrated eroding agent which erodes the metal layer 20. The erosion of metal layer 20 is followed by passage of drug which is contained within reservoir 12.

Figure 5:
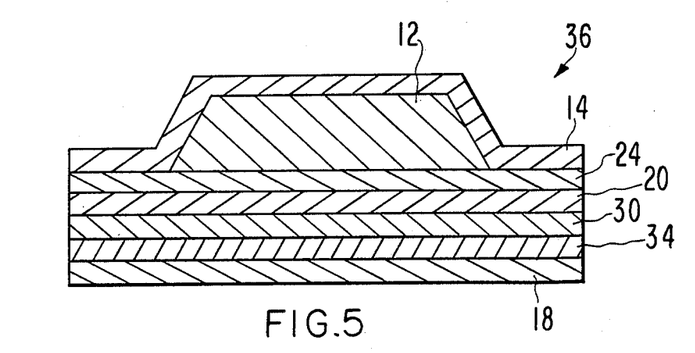
FIG. 5 is a schematic cross-sectional view of another embodiment of this invention, having the eroding agent combined with the adhesive and having an eroding agent rate controlling membrane.

An alternate embodiment of the invention is shown in FIG. 5. System 36 is a modification of system 32 (FIG. 4) but has the same basic components and arrangement. The distinction of this embodiment is the presence of an eroding agent rate controlling membrane 30, positioned between the contact adhesive/eroding agent layer 34 and metal layer 20.

Figure 6:
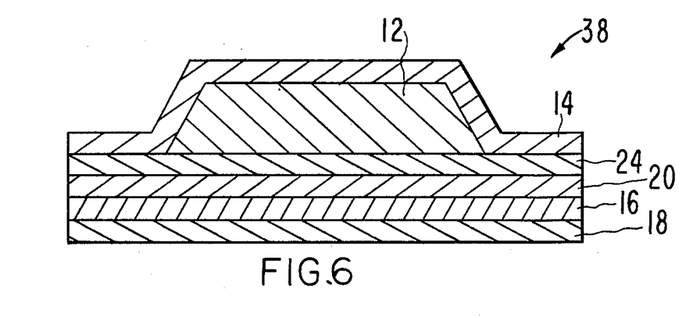
FIG. 6 is a schematic cross-sectional view of another embodiment of this invention, utilizing sweat as an activating means.

Another embodiment of the delivery device of this invention is shown in FIG. 6 as system 38. In this embodiment, the activating means is not incorporated into the system. Rather, the activating means is sweat, available from the biological environment. Sweat contains a certain amount of sodium chloride, which acts as an eroding agent, as it has been known to cause an electrolytic reaction with nickel and nickel containing alloys. J. D. Hemingway and M. M. Molokhia, "The Dissolution of Metallic Nickel in Artificial Sweat", CONTACT DERMATITIS 16, pg. 99-105 (1987).

In operation, release liner 18 is removed and system 38 positioned on the skin. Sweat available from the skin diffuses through the adhesive 16 and reacts with the metal layer 20, causing it to erode thus allowing for passage of drug from reservoir 12.

Figure 7:
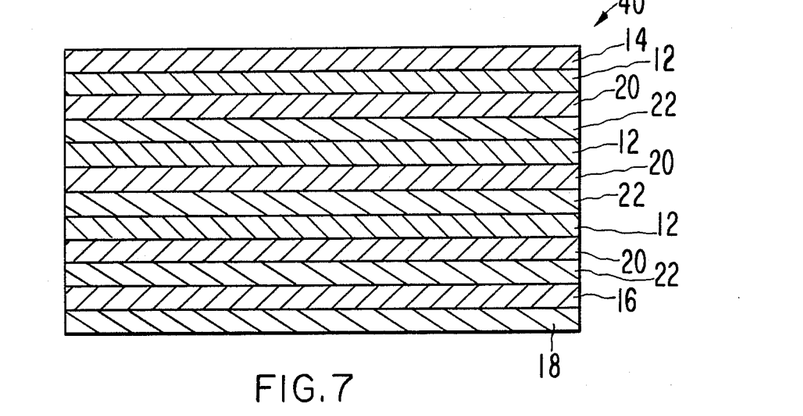
FIG. 7 is a schematic cross-sectional view of another embodiment of this invention, which provides pulsed delivery.

The devices thus far described in FIGS. 1 and 3-6, are single pulse delivery systems. This invention can also be used to provide multipulsed drug delivery by means of a relatively thin and multilaminate system 40, as is illustrated in FIG. 7. System 40 is provided with a plurality of activating means 22, metal layers 20 and drug reservoirs 12.

For each reservoir layer implemented there is one pulse. System 40 as shown, will provide three pulses of drug delivery. However, this number is merely illustrative and more layers may be incorporated. The system may have a single drug rate controlling membrane positioned between the reservoir 12 and metal layer 20 closest to the skin. The system may also have one or more eroding agent rate controlling membranes positioned between the metal layers 00 and activating means 22. The desire for rate control of the drug and/or the eroding agent must be balanced with the fact that the presence of a rate controlling membrane increases resistance to passage and this is a cumulative 25 effect when dealing with a system having a plurality of layers such as is the case with system 40.

In operation, moisture migrates through adhesive layer 16 and enters the first activating means 22. The hydrated eroding agent then contacts the first metal layer 20, eroding it to allow passage of drug from reservoir 12 by means of diffusion. When the drug is depleted from the first reservoir, moisture migrates to the second activating means and the erosion process is repeated. As the second and subsequent metal layers are being eroded, there is a lapse in drug delivery, thus providing a pulsed system.

The duration of drug delivery is determined by the amount of drug loaded into the respective reservoirs and the duration of the lapse time is determined by the rate at which the respective metal layers are eroded. The embodiment of FIG. 7 is especially suited for a nitroglycerin regimen with, for example, a metal layer of magnesium or aluminum, and a slightly acidic eroding agent contained within the activating means.

Figure 8:
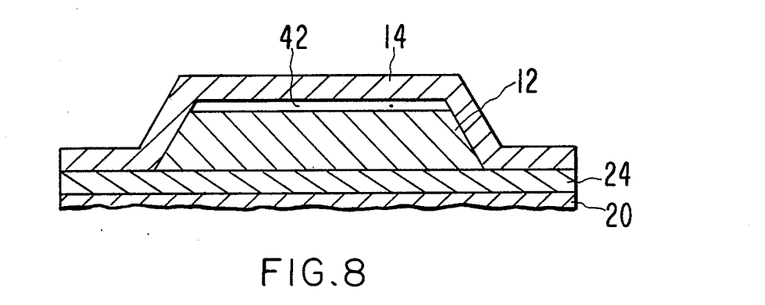
FIG. 8 is a schematic partial cross-sectional view of an embodiment of this invention having a head space.

The metal layer 20, of the aforementioned embodiments, when eroded, especially by the process of oxidation, may generate a gas, specifically, hydrogen. The embodiments of this invention may be modified to handle any gas that may be evolved during erosion. The system may be equipped with a head space 42, as shown in FIG. 8. In a form-fill-seal system such as those shown in FIGS. 1 and 3-6, the head space can be introduced into the pouch as a bubble when the pouch is filled with gel.

Alternately, a hole or vent can be made in the backing layer and covered with a tab to be removed immediately prior to application to the delivery surface. If an adhesive overlay is used to position the system on the surface, a gas permeable material can be used such as spun-bonded polyethylene film, commercially available as Tyveck® from E. I. DuPont de Nemours and Company, Inc.

EXAMPLE II

A system 10 can be designed in accordance with FIG. 1, wherein the reservoir 12 is comprised of a therapeutic agent dispersed throughout an EVA 40 polymeric matrix. The system can have a MEDPAR® backing 14 and a pharmaceutically acceptable in-line contact adhesive layer 16.

The delay portion of system 10 would be comprised of a polyvinylacetate rate controlling membrane 24, thinly coated with a magnesium layer 20. The activating means 22 would be comprised of citric acid (eroding agent) dispersed throughout an EVA 40 polymeric matrix.

In operation, moisture migrates into layer 22, reacting with the citric acid to generate hydrogen ions.

This particular embodiment provides for erosion of the metal layer by an oxidation-reduction reaction where hydrogen ions (H+) migrate to the magnesium layer-activating means interface 26. There, the metal (Mg) is oxidized (Mg++) and the hydrogen reduced, which then evolves as a gas (H$_2$), by the following oxidation-reduction reactions, where the citric acid readily attacks the magnesium layer:

This oxidation-reduction reaction results in the erosion of the metal (Mg) layer 20, which allows for passage of the drug, and therefore the onset of drug delivery.

EXAMPLE III

A system can be designed similar to that of Example II, however using cupric sulfate as the eroding agent, so that when moisture migrates into activating means 22, the reaction would generate copper and sulfate ions. As with Example II, the metal layer is eroded by an oxidation-reduction reaction.

The copper ions (Cu++) then migrate to the magnesium layer 20, where the metal (Mg) is oxidized (Mg++) and the copper ions are reduced, forming a deposit (Cu) on the metal layer-activating means interface 26.

The oxidation-reduction reactions are as follows:

As stated in Example I, this oxidation-reduction reaction results in erosion of the metal layer 20, providing for drug passage and delivery.

EXAMPLE IV

A system 32 can be designed in accordance with FIG. 4, wherein the drug reservoir 12 is comprised of a therapeutic agent dispersed throughout an EVA 40 polymeric matrix. The system can have a MEDPAR® backing 14.

The delay portion of system 32 is comprised of an EVA 12 rate controlling membrane 24 thinly coated with an aluminum metal layer 20, and a contact adhesive/eroding agent layer 34 comprised of sodium carbonate and a copper compound such as CuCl$_2$ or CuSO$_4$.

In operation, moisture migrates into layer 34 reacting with the copper compound (CuCl$_2$ or CuSO$_4$, for example) to generate copper ions. These ions (Cu++) then migrate to the metal layer/ activating means interface 26, where the aluminum is oxidized (Al+++) and the copper ions are reduced to form a deposit (Cu) on the metal layer.

The oxidation-reduction reactions are as follows:

EXAMPLE V

A system can be designed identical to that of Example IV but utilizing a zinc metal layer 20. Zinc is readily soluble in dilute acids and a suitable eroding agent such as citric acid is incorporated into the contact adhesive/eroding agent layer 34.

Moisture migrates into the layer 34 reacting with the citric acid contained therein to generate hydrogen ions (H+). These ions migrate to the metal layer 20 where the zinc is oxidized (Zn++) and the hydrogen reduced and evolved as a gas (H₂) by the following oxidation-reduction reactions:

Having thus described our invention and described in detail certain preferred embodiments thereof, it will be readily apparent that various modifications to the invention may be made by workers skilled in the art without departing from the scope of this invention, which is limited only by the following claims.

What is claimed is:

1. A controlled release medical device for delivery of a drug in a pre-determined delivery rate pattern to a biological environment comprising, in combination:
   reservoir means containing said drug having a surface through which the drug is released to the biological environment;
   a metal layer disposed between said reservoir means and the biological environment, wherein said metal layer in a first state is uneroded and, is substantially impermeable to the passage of said drug, and in a second stat is eroded and permeable to said drug;
   whereby substantially all of said drug must pass through said metal layer to reach the biological environment, and whereby the passage of drug to the biological environment by diffusion is impeded until the metal layer changes state.

2. The device of claim wherein said activating means is substantially free of said drug.

3. The device of claim 1 further comprising activating means by which said metal layer is changed from an uneroded state to an eroded state.

4. The device of claim 1 which further comprises:
   rate controlling means for controlling the rate at which drug is release from said reservoir.

5. The device of claim 4 wherein said metal layer, in the first uneroded state, is impermeable to the passage of drug in said reservoir means and permeable to the drug when in a second and eroded state and wherein said activating means is comprised of an eroding agent which converts said metal layer from its first to its second state.

6. The device of claim 5 which further comprises:
   rate controlling means for controlling the rate at which eroding agent is released from said activating means.

7. The device of claim 4 wherein said metal layer, in the first uneroded state, is impermeable to the passage of drug in said reservoir means and permeable to the drug when in a second and eroded state and wherein said activating means is sweat.

8. The device of claim 3 which further comprises:
   a plurality of metal layers, each disposed between a reservoir means and an activating means.

9. The device of claim 1 which further comprises:
   means for collecting any gas evolved as said metal changes state.

10. The device of claim 1 wherein drug is selected from the group consisting of nitroglycerin, benztropine, nicotine, secoverine, propranolol and timolol.

11. A medical device for the percutaneous administration of a drug, comprising:
    a backing layer impermeable to said drug;
    an drug reservoir comprised of said drug, disposed between said backing layer and the skin;
    an activating means disposed between said reservoir and the skin;
    a metal layer disposed between the reservoir and said activating means, wherein said metal layer is impermeable to the passage of said drug when uneroded and permeable to said drug when eroded; and
    a means for maintaining said device in drug transferring relationship to the skin.

12. The device of claim 11 wherein said activating means is substantially free of said drug.

13. The device of claim 11 which further comprises:
    a rate controlling means for controlling the rate at which said drug is released from said drug reservoir when the device is placed in contact with the skin.

14. The device of claim 11 which further comprises:
    a rate controlling means for controlling the rate at which said eroding agent is released from said activating means.

15. The device of claim 11 wherein said drug is selected from the group consisting of nitroglycerin, benztropine, nicotine, secoverine, propranolol and timolol.

16. A method of delivering a drug to a biological environment, comprising the steps of:
    placing a reservoir containing a drug to be delivered at the biological environment; and
    interposing a substantially drug free activating means and metal layer between the reservoir and the biological environment, wherein the metal layer in an un-eroded state is impermeable to the passage of said drug and in an eroded state is permeable to said drug.

* * * * *